United States Patent [19]

Nakashima et al.

[11] Patent Number: 5,219,854
[45] Date of Patent: Jun. 15, 1993

[54] BLOOD PLATELET-DECREASING METHOD

[75] Inventors: Mitsuyoshi Nakashima, Hamamatsu; Nobuyuki Kikuchi; Misao Miyamoto, both of Tokyo, all of Japan

[73] Assignees: Nissan Chemical Industries Ltd.; Zeria Pharmaceutical Co., Ltd., both of Tokyo, Japan

[21] Appl. No.: 907,637

[22] Filed: Jul. 2, 1992

[30] Foreign Application Priority Data

Jul. 5, 1991 [JP] Japan .................. 3-165670

[51] Int. Cl.$^5$ ............................. A61K 31/50
[52] U.S. Cl. .................................. 514/247
[58] Field of Search ........................ 514/247

[56] References Cited

U.S. PATENT DOCUMENTS 4,892,947  1/1990  Mutsukado et al. ............ 514/247
4,978,665 12/1990  Tanikawa et al. ............. 514/247

FOREIGN PATENT DOCUMENTS 0201765 11/1986 European Pat. Off.

OTHER PUBLICATIONS

Japanese Journal of Pharmacology, vol. 56, No. 1, May 1992, pp. 79–84, A. Yamamoto, et al., "Effects of NZ-107 on Tracheal Responses to Adenosine in the Guinea Pig".

Japanese Journal of Pharmacology, vol. 43, No. 2, Feb. 1991, pp. 83–87, A. Yamamoto, et al., "Effect of an Anti-SRS-A Agent, NZ-107, on Airway Responses Induced by Ovalbumin and A23187 in the Guinea-Pig".

Primary Examiner—Frederick E. Waddell
Assistant Examiner—William Jarvis
Attorney, Agent, or Firm—Oblon, Spivak, McClelland, Maier & Neustadt

[57] ABSTRACT

A blood platelet-decreasing therapeutic drug comprising as an effective ingredient a 3(2H)-pyridazinone compound of the formula (I):

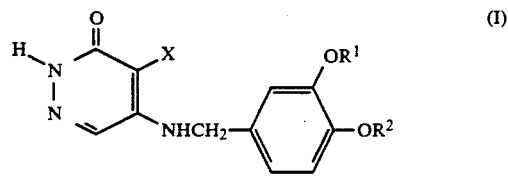

wherein each of $R^1$ and $R^2$, which are independent of each other, is a hydrogen atom or a $C_{1-4}$ alkyl group, and X is a chlorine atom or a bromine atom, or a pharmaceutically acceptable salt thereof.

2 Claims, No Drawings

BLOOD PLATELET-DECREASING METHOD

The present invention relates to a blood platelet-decreasing therapeutic drug. More specifically, it relates to a blood platelet-decreasing therapeutic drug comprising as an effective ingredient a 3(2H)-pyridazinone compound of the formula (I):

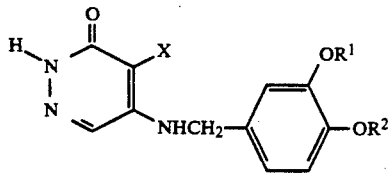

wherein each of $R^1$ and $R^2$, which are independent of each other, is a hydrogen atom or a $C_{1-4}$ alkyl group, and X is a chlorine atom or a bromine atom, or a pharmaceutically acceptable salt thereof.

3(2H)-pyridazinone compounds of the formula (I) of the present invention are covered by the compounds disclosed in Japanese Unexamined Patent Publication No. 30769/1987, Canadian Patent No. 1,290,336, European Patent No. 201,765 and U.S. Pat. No. 4,892,947 which disclose methods for their preparation and describe that such compounds show anti-SRS-A activities and are useful as antiasthmatic agents or antiallergic agents.

On the other hand, a drug which specifically decreases a blood platelet count and has high safety, has been expected to be useful as a prophylactic or therapeutic drug against several diseases for which medically useful drugs are few at present.

Namely, as the diseases to which the blood platelet-decreasing drug is expected to be applied, there may be first mentioned diseases wherein the blood platelet count abnormally increases. As the specific examples thereof, diseases such as thrombocytosis and chronic myelogenous leukemia may be mentioned.

Another diseases to which the drug of the present invention is expected to be applied are diseases in which activated blood platelets take part in the outset and evolution of acosmia. As the specific examples of such application, there may be mentioned the use for various thromboses and the use for the purpose of preventing postoperative reobstruction of blood vessel formation conducted as an operative therapy therefor.

Further, it is also suggested that blood platelets take part in glomerulophrosis and cancer metastasis (Journal of Royal College of Physicians, vol. 7, pages 5 to 18, 1972; International Journal of Cancer, vol. 40, pages 525 to 531, 1987). In fact, in the animal test models of them, effects by the blood platelet-decreasing activities using an antiplatelet antibody are reported (Nichijinshi, vol 28, pages 115 to 126, 1986; Cancer Research, vol. 44, pages 3,884 to 3,887, 1984).

In spite of the expectation that the blood platelet-decreasing drug becomes a medically useful drug, there has been hardly reported a drug which specifically decreases only blood platelets and has a high safety (Thrombosis Haemostasis, vol. 52, pages 325 to 328, 1984).

The present inventors have conducted extensive studies on various pharmacological activities with respect to a series of 3(2H)-pyridazinones, and have unexpectedly found that specific compounds represented by the formula (I) are drugs which specifically decrease human blood platelets and show high safety, and accordingly can be used as a blood platelet-decreasing drug. The present invention has been accomplished on the basis of this discovery.

Thus, the present invention provides a medical drug useful as a prophylactive or therapeutic drug against diseases wherein blood platelet count abnormally increases or activated blood platelets take place in the outset and evolution of the acosmia, for example, thrombocytasis, chronic myelogenous leukomia, various thrombotic diseases and prevention of postoperative reobstruction of blood vessel formation used for operative therapy thereof, glomerulonephrosis and cancer metastasis, etc.

The present invention provides a blood platelet-decreasing therapeutic drug comprising as an effective ingredient a 3(2H)-pyridazinone compound of the formula (I):

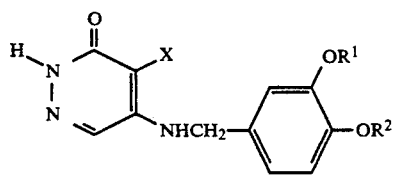

wherein each of $R^1$ and $R^2$, which are independent of each other, is a hydrogen atom or a $C_{1-4}$ alkyl group, and X is a chlorine atom or a bromine atom, or a pharmaceutically acceptable salt thereof.

In the formula (I), each of $R^1$ and $R^2$, which are independent of each other, is a hydrogen atom, a methyl group, an ethyl group, a normal propyl group, an isopropyl group, a normal butyl group, an isobutyl group or a tertiary butyl group, and X is a chlorine atom or a bromine atom.

Particularly preferred is 4-bromo-5-(3-ethoxy-4-methoxybenzylamino)-3(2H)-pyridazinone.

The compound of the formula (I) can be readily produced by the methods as described in Japanese Unexamined Patent Publication No. 30769/1987, Canadian Patent No. 1,290,336, European Patent No. 201,765 and U.S. Pat. No. 4,892,947.

As the manner of administration of the 3(2H)-pyridazinone compounds of the formula (I) or their pharmaceutically acceptable salts of the present invention, there may be mentioned a non-oral administration in the form of injections (subcutaneous, intravenous, intramuscular or intraperitoneal injection), ointments, suppositories or aerosols, or an oral administration in the form of tablets, capsules, granules, pills, syrups, liquids, emulsions or suspensions.

The above pharmaceutical composition contains the compound of the present invention in an amount of from 0.1 to 99.5% by weight, preferably from 0.5 to 95% by weight, based on the total weight of the composition.

The clinical dose of the compound of the present invention varies depending upon the age, the body weight, the sensitivity or the symptom, etc. of the patient. However, the effective daily dose is usually from 1 to 1,500 mg, preferably from 1 to 200 mg, for an adult.

However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as hydroxypropyl cellulose, syrups, gum arabic, gelatin, sorbitol, tragacant gum, methyl cellulose or polyvinylpyrrolidone; a disintegrant such as starch, carboxylmethyl cellulose or its calcium salt, crystal cellulose powder or polyethylene glycol; a gloss agent such as talc, magnesium or calcium stearate or colloidal silica; or a lubricant such as sodium laurate or glycerol.

The injections, solutions, emulsions, suspensions, syrups or aerosols, may be prepared by using a solvent for the active ingredient such as water, ethyl alcohol, isopropyl alcohol, propylene glycol, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl cellulose, a cellulose derivative such as methyl cellulose, or a natural rubber such as tragacant gum or gum arabic; or a preservative such as a paraoxy benzoic acid ester, benzalkonium chloride or a salt of sorbic acid.

For the ointment as a percutaneous-absorptive type formulation, there may be used, e.g. white vaseline, liquid paraffin, a higher alcohol, macrogoal ointment, a hydrophilic ointment or an aqueous gel base meterial.

The suppositories may be prepared by using e.g. cocoa butter, polyethylene glycol, lanolin, fatty acid triglyceride, coconut oil or polysorbate.

These compounds have low toxicities and thus may be sufficiently used for medical products. For example, the 50% lethal dose ($LD_{50}$) in the acute toxicity tests after single oral administration of 4 brome-5-(3-ethoxy-4-methoxybenzylamino)-3(2H)-pyridazinone as a typical compound thereof, was 2,000 mg/kg with respect to each of mouse (ICR strain, 6 weeks old), rat (SD strain, 6 weeks old) and dog (beagle, 6 months old).

Now, the present invention will be described in further detail with reference to Test Examples and Formulation Examples. However, the present invention is by no means limited to those Examples.

TEST EXAMPLES

To each of six healthy adult males (23 to 32 years age, average: 28 years age), two tablets each containing 20 mg of 4-bromo-5-(3-ethoxy-4-methoxybenzylamino)-3(2H)-pyridazinone (Compound A) were orally administered (40 mg) three times a day (120 mg) in the morning, noon and evening for 7 days (on the 7th day, administered only in the morning). Examinations were conducted with respect to the following four items from the time before the administration to the time until the 29th day after the termination of administration.

1) SUBJECTIVE SYMPTOMS

Everyday during the period of examination, each testee records the subjective symptoms.

2) DIAGNOSIS BY DOCTOR

A doctor makes diagnoses by asking, or ansculating and percussioning, and records his observations.

3) SCIENTIFIC EXAMINATION

Blood pressure, pulse rate, body temperature, breathing rate, ECG (12 derivatives), pulmonary function (FVC, $FEV_{1.0\%}$), and visual or acoustic observation

4) CLINICAL EXAMINATION (1) Hematological Examination

Erythrocyte count, leukocyte count, hemoglobin quantity, hematocrit value, blood platelet count, reticulocyte count, leukocyte fraction and prothrombin time (2) Hematological Biochemistry Examination Total protein, albumin, A/G ratio (protein fraction), BUN, creatinine, uric acid, total cholesterol, neutral fats, Na, K, Cl, Al-P, LAP, GOT, GPT, LDH, γ-GTP, ZTT, TTT, CPK, total bilirubin, direct bilirubin and blood sugar (3) Urine Examination Specific gravity, pH, bilirubin, urobilinogen, ketone body, sugar, protein and sedimentation In the above-mentioned items of examinations, no problematic symptom or change has been observed during the period of examinations with respect to all items of examinations other than the blood platelet count.

Table 1 shows the change of blood platelet count during the period of examinations in terms of an average value ± a standard deviation.

TABLE 1

| Change of blood platelet count at the time of repeated administration of Compound A | |
|---|---|
| The time of measurement | An average value ± a standard deviation ($\times 10^4/\mu l$) |
| Before the initiation of administration | 27.6 ± 2.6 |
| 3 days after the initiation of administration | 25.0 ± 2.7** |
| 1st day after the termination of administration | 14.1 ± 2.0*** |
| 6th day after the termination of administration | 20.4 ± 2.2** |
| 29th day after the termination of administration | 29.2 ± 3.9 |

Statistical significance to the value before administration (paired t-test)
*$p < 0.001$, $p < 0.01$

FORMULATION EXAMPLE 1

| Tablets | |
|---|---|
| Compound A | 10 g |
| Lactose | 20 g |
| Starch | 4 g |
| Starch for paste | 1 g |
| Magnesium stearate | 100 mg |
| Carboxymethyl cellulose calcium (CMC-Ca) | 7 g |
| Total | 42.1 g |

The above components were mixed in a usual manner, and formulated into sugar-coated tablets each containing 20 mg of an active ingredient.

FORMULATION EXAMPLE 2

| Capsules | |
| --- | --- |
| Compound A | 10 g |
| Lactose | 20 g |
| crystal cellulose powder | 10 g |
| Magnesium stearate | 1 g |
| Total | 41 g |

The above components were mixed in a usual manner, and filled into gelatin capsules to obtain capsules each containing 20 mg of an active ingredient.

FORMULATION EXAMPLE 3

| Soft capsules | |
| --- | --- |
| Compound A | 10 g |
| Corn Oil | 35 g |
| Total | 45 g |

The above components were mixed and formulated in a usual manner to obtain soft capsules.

FORMULATION EXAMPLE 4

| Ointment | |
| --- | --- |
| Compound A | 1.0 g |
| Olive oil | 20 g |
| White vaseline | 79 g |
| Total | 100 g |

The above components were mixed in a usual manner to obtain 1% ointment.

FORMULATION EXAMPLE 5

| Aerosol suspension | |
| --- | --- |
| (A) Compound A | 0.25% |
| Isopropyl myristate | 0.10% |
| Ethanol | 26.40% |
| (B) A 60-40% mixture of 1,2-di- | 73.25% |
| chlorotetrafluoroethane and 1-chloropentafluoroethane | |

The above composition (A) was mixed. The solution mixture thereby obtained was charged in a container equipped with a valve, and the propelolant (B) was injected from a valve nozzle to a gauge pressure of from about 2.46 to 2.81 mg/cm$^2$ at 20° C. to obtain an aerosol suspension.

As described above, it is clear that the compound of the present invention shows substantially no side-effect and specifically decreases the blood platelet count in a human body, and that the activity disappears relatively fast after the administration is terminated. Accordingly, the compound of the present invention is useful as a blood platelet-decreasing therapeutic drug such as a prophylactic or therapeutic drug against diseases wherein blood platelet count abnormally increases or diseases wherein activated blood platelets take part in the outset and evolution thereof.

We claim:

1. A method for decreasing the blood platelet level of a subject in need thereof which comprises administering to the subject an effective amount of a blood platelet-decreasing therapeutic drug comprising as an effective ingredient a 3(2H)-pyridazinone compound of the formula (I):

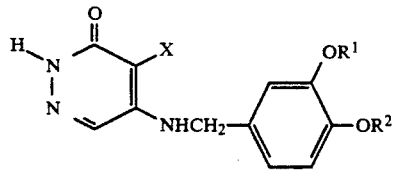

wherein each of $R^1$ and $R^2$, which are independent of each other, is a hydrogen atom or a $C_{1-4}$ alkyl group, and X is a chlorine atom or a bromine atom, or a pharmaceutically acceptable salt thereof.

2. The method according to claim 1, wherein $R^1$ is an ethyl group, $R^2$ is a methyl group and X is a bromine atom.

* * * * *